United States Patent [19]

Mrozik et al.

[11] Patent Number: 4,895,837
[45] Date of Patent: Jan. 23, 1990

[54] AVERMECTIN DERIVATIVES

[75] Inventors: Helmut Mrozik, Matawan; Frank S. Waksmunski, South River, both of N.J.

[73] Assignee: Merck & Co., Inc., Rahway, N.J.

[21] Appl. No.: 296,172

[22] Filed: Jan. 13, 1989

Related U.S. Application Data

[63] Continuation-in-part of Ser. No. 150,186, Jan. 29, 1988, abandoned.

[51] Int. Cl.$^4$ ............... A61K 31/70; C07H 17/04; C07P 313/06
[52] U.S. Cl. .................... 514/30; 536/7.1; 549/264; 71/88; 514/450
[58] Field of Search ............ 536/7.1; 514/30, 450; 549/264; 71/88

[56] References Cited

U.S. PATENT DOCUMENTS 4,199,569  4/1980  Chabala et al. ............... 536/7.1
4,310,519  1/1982  Albers-Schonberg et al. ...... 536/7.1
4,550,160  10/1985  Mrozik ........................ 536/7.1

Primary Examiner—Herbert J. Lilling
Assistant Examiner—Elli Peselev
Attorney, Agent, or Firm—David L. Rose; Hesna J. Pfeiffer

[57] ABSTRACT

There are disclosed novel avermectin Δ 23,24-derivatives (also referred to as 23,24-dehydro compounds). The compounds are prepared by selective dehydration of avermectin A2 or B2 compounds. The avermectin compounds have utility as anti-parasitic agents and compositions for that use are also disclosed. The compounds are also highly potent insecticides against agricultural pests. The Δ 23,24-avermectin compounds have increased activity relative to the A2 or B2 compounds.

15 Claims, No Drawings

AVERMECTIN DERIVATIVES

CROSS REFERENCE TO RELATED APPLICATIONS

This application is a continuation-in-part or our application Ser. No. 150,186, filed Jan. 29, 1988 now abandoned.

BACKGROUND OF THE INVENTION

The term avermectin (previously referred to as C 076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The avermectin compounds are a series of macrolides, each of which is substituted thereon at the 13 position with a 4'-(α-L-oleandrosyl)-α-L-oleandrose group. The avermectin compounds and the instant derivatives thereof have a very high degree of anthelmintic and anti-parasitic activity.

Also included in the prior art are certain synthetically modified avermectins such as 22,23-dihydro avermectin B1a/B1b also known as ivermectin disclosed in U.S. Pat. No. 4,199,569.

The avermectin series of compounds, which are isolated from a fermentation broth, have the following structure:
   wherein R is the 4'-(α-L-oleandrosyl)-α-L-oleandrose group of the structure:

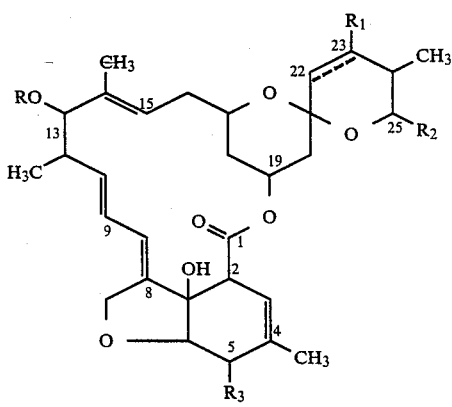

wherein R is the 4'(α-L-oleandrosyl)-α-L oleandrose group of the structure:

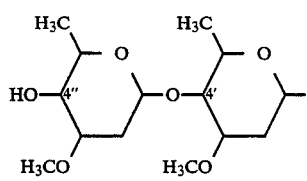

and wherein the broken line indicates a single or a double bond; $R_1$ is hydroxy and is present only when said broken line indicates a single bond;
   $R_2$ is iso-propyl or sec-butyl; and
   $R_3$ is methoxy or hydroxy.

There are eight different major avermectin natural product compounds and they are given the designations A1a, A1b, A2a, A2b, B1a, B1b, B2a and B2b based upon the structure of the individual compounds.

In the foregoing structural formula, the individual avermectin compounds are as set forth below. (The R group is 4'(α-L-oleandrosyl)-α-L-oleandrose):

|     | $R_1$              | $R_2$     | $R_3$   |
| --- | ------------------ | --------- | ------- |
| A1a | (22,23-Double Bond) | sec-butyl | —OCH$_3$ |
| A1b | (22,23-Double Bond) | iso-propyl | —OCH$_3$ |
| A2a | —OH                | sec-butyl | —OCH$_3$ |
| A2b | —OH                | iso-propyl | —OCH$_3$ |
| B1a | (22,23-Double Bond) | sec-butyl | —OH     |
| B1b | (22,23-Double Bond) | iso-propyl | —OH     |
| B2a | —OH                | sec-butyl | —OH     |
| B2b | —OH                | iso-propyl | —OH     |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

The 13-deoxy avermectin aglycone compounds, which lack the 13-disaccharide group are also starting materials for the instant compounds. They are disclosed in U.S. Pat. Nos. Re. 32,006 and 32,034.

The avermectin B1 and 22.23 dihydro avermectin B1 compounds are of superior activity and mixtures of the a and b compounds have been selected to be marketed for their broad spectrum antiparasitic activity against both animal and plant parasites. The avermectin A2 and B2 compounds are of a considerably lower level of activity and are not marketed products. However, the conversion of the A2 and B2 compounds to the 23-deoxy-Δ23,24-avermectin compounds produces compounds of significantly higher levels of activity. Thus, the A2 and B2 compounds, which would normally be discarded in the preparation of the B1 and 22,23-dihydro B1 compounds, are utilized in the preparation of compounds with levels of activity commensurate with marketed products.

SUMMARY OF THE INVENTION

The instant invention is concerned with certain derivatives of avermectin compounds wherein the 23 hydroxy group of avermectin A2 and B2 compounds is selectively eliminated to form 23-deoxy-23,24-bis-dehydro compounds of significant levels of anti-parasitic activity. Thus it is an object of the instant invention to describe such avermectin elimination products. A further object is to describe processes for the preparation of such compounds. A still further object is to describe the uses of such compounds as anti-parasitic and insecticidal agents. Still further objects will become apparent from a reading of the following description.

DESCRIPTION OF THE INVENTION

The compounds of the instant invention have the following structural formula.

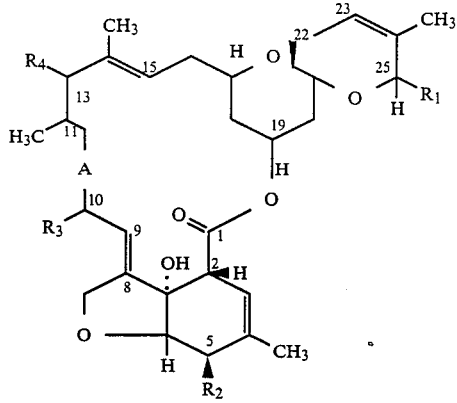

wherein A represents a single bond or a double bond,
R₁ is iso-propyl or sec-butyl;
R₂ is hydroxy, ketone, loweralkoxy, or protected hydroxy;
R₃ is hydrogen, halogen, or ketone, however R₃ is present only when A represents a single bond;
R₄ is hydrogen, hydroxy, halogen,

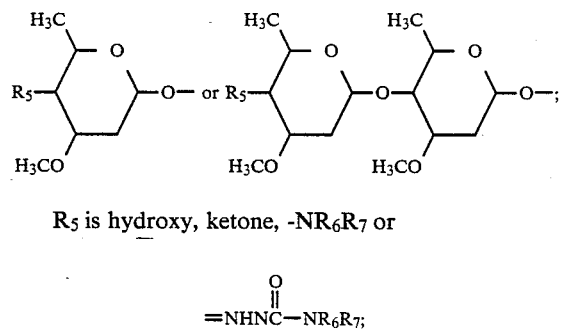

R₅ is hydroxy, ketone, -NR₆R₇ or $$=NHN\overset{O}{\overset{\|}{C}}-NR_6R_7;$$

and
R₆ and R₇ are independently hydrogen, loweralkyl or loweralkanoyl.

In the instant description, the term "loweralkyl" is intended to include those alkyl groups containing from 1 to 6 carbon atoms in either a straight or branched chain or a cyclic configuration of from 3 to 6 carbon atoms. Exemplary of such alkyl groups are methyl, ethyl, propyl, isopropyl, butyl, sec-butyl, pentyl, hexyl, cyclopentyl, cyclohexyl and the like.

The term "loweralkanoyl" is intended to include those alkanoyl groups of from 2 to 6 carbon atoms of either a straight or branched chain. Such groups are exemplified by acetyl, propionyl, butyryl, pentanoyl, hexanoyl and the like.

The term "halogen" is intended to include the halogen atom, fluorine, chlorine, bromine and iodine.

Preferred compounds of this invention are realized in the above structure wherein: A is a single, or a double bond; R₁ is isopropyl, or sec-butyl; R₂ is hydroxy; R₃ is hydrogen, halogen, hydroxy or oxo; R₄ is hydrogen, hydroxy, halogen, 4'-R₅-(α-L-oleandrosyloxy), 4"-R₅-[4'-(α-L-oleandrosyl)-α-L-oleandrosyloxy; and R₅ is hydroxy, amino loweralkylamino, diloweralkylamino, Additional preferred compounds are realized when R₄ is halogen, and in particular, when R₄ is fluorine, and R₁, R₂, R₃ and R₅ are as defined above Examples of preferred compounds of this invention are realized in the following:

23,24-dehydro avermectin B2a/B2b
23,24-dehydro avermectin A2a/A2b
23,24-dehydro avermectin B2a/B2b aglycone
23,24-dehydro avermectin B2a/B2b monosaccharide
23,24-dehydro-13-deoxy avermectin B2a/B2b aglycone
23,24-dehydro-10,11-dihydro avermectin B2a/B2b
23,24-dehydro-10,11-dihydro avermectin B2a/B2b monosaccharide
23,24-dehydro-10,11-dihydro avermectin B2a/B2b aglycone
23,24-dehydro-13-deoxy-10,11-dihydro avermectin B2a/B2b aglycone
23,24-dehydro-10,11-dihydro-10-fluoro avermectin B2a/B2b
23,24-dehydro-10,11-dihydro-10-fluoro avermectin B2a/B2b monosaccharide
23,24-dehydro-10,11-dihydro-10-fluoro avermectin B2a/B2b aglycone
23,24-dehydro-13-deoxy-10,11-dihydro-10-fluoro avermectin B2a/B2b aglycone
23,24-dehydro 4"-deoxy-4"-methylamino avermectin B2a/B2b
23,24-dehydro 4"-deoxy-4"-amino avermectin B2a/B2b
23,24-dehydro 4"-deoxy-4"-dimethylamino avermectin B2a/B2b
23,24-dehydro 4"-oxo avermectin B2a/B2b semicarbazone
23,24-dehydro 4"-oxo avermectin B2a/B2b(4-methyl-semicarbazone)
23,24-dehydro 4"-oxo avermectin B2a/B2b(4,4-dimethyl-semicarbazone)
23,24-dehydro-13-deoxy-13-fluoroavermectin B2a/B2b aglycone The "b" compounds, those with a 25-iso-propyl group, are somewhat difficult to separate from the corresponding "a" compound with a 25-sec-butyl group and as such the compounds are generally isolated as mixtures of the two compounds. Thus references in the instant application to "a" compounds such as B1a, A1a, and the like, are construed to define the pure compound as well as those which actually contain a certain proportion of the corresponding "b" compound.

Alternatively, this representation of a mixture is sometimes done by referring, for example, to "the B1 or B2 compounds" or by separating the "a" compound from the "b" compound by a slash (/) such as B1a/B1b, B2a/B2b and the like.

The compounds of the instant invention differ from other avermectin compounds in that the 23-hydroxy compounds, A2 and B2 compounds are converted into 23-dehydroxy-Δ23,24 compounds. Such compounds are significantly superior to the A2 and B2 starting materials in their antiparasitic activity.

The instant compounds are prepared from the suitably protected avermectin A2 or B2 compound, that is a compound with an unprotected 23-hydroxy group but with all other hydroxy groups protected. This compound is treated with the reagent diethylamino sulfurtrifluoride, generally referred to as DAST. This reagent is generally known in the art as a fluorinating reagent, however when used under the below described conditions and on the instant compounds, there is observed the surprising result that no fluoridation occurs anywhere on the avermectin molecule. The unprotected 23-hydroxy group is removed and a 23-24 double bond (Δ23,24) is formed.

The reaction is represented in the following reaction scheme.

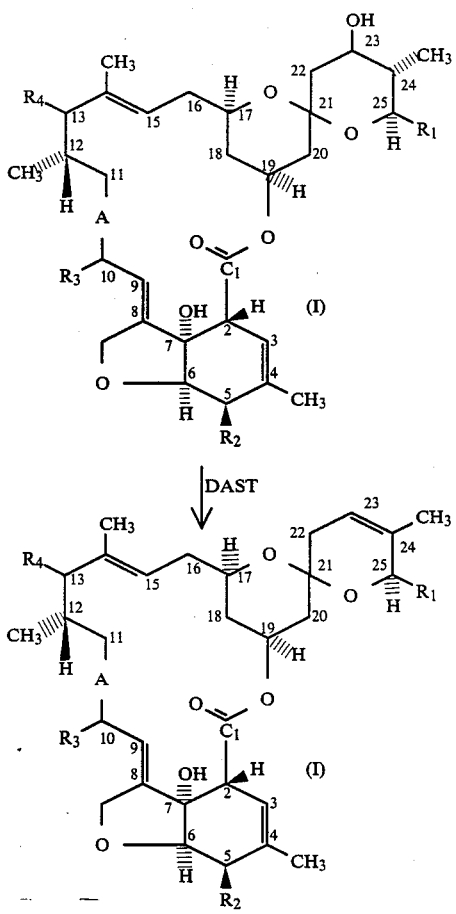

The reaction is carried out initially at a reduced temperature due to the reactivity of DAST. Generally temperatures of from −50° C. to −100° C. are utilized. It is preferred to carry out the reaction at about −78° C. since this is the temperature which is achieved by placing the reaction vessel in a dry-ice (solid carbon dioxide-acetone) bath. To further avoid side-reactions, the reaction is preferably carried out under a blanket of nitrogen an other inert atmosphere. The reaction is maintained at the reduced temperatures from 10 to 120 minutes and then is generally raised to room temperature slowly, over a period of from 60 to 180 minutes. To complete the reaction, the reaction vessel may be maintained at room temperature for from 1 to 8 hours or until analysis of aliquots of the reaction mixture indicate that the reaction is complete. Generally analytical procedures which can follow the disappearance of the 23-hydroxy group will give a good indication of the degree to which the reaction has progressed to completion. The product is isolated using standard techniques known to those skilled in the art and the protecting groups are removed following the procedures described below.

PREPARATION OF STARTING MATERIALS

The ultimate starting materials for the compounds of this invention are the avermectin fermentation products defined above which have the isopropyl or sec-butyl group at the 25 position. Thus it is apparent that additional reactions are required to prepare many of the immediate starting materials for the instant compounds. Specifically, reactions are carried out at the 4', 4", 5', 10, 11 and 13, positions. In addition, during the various reactions described above, and below it may be necessary to protect various reactive groups to prevent the undesired reaction of such groups. In addition, protection of such reactive groups may facilitate the separation of the various products. With the appropriate positions protected, the DAST reaction may be carried out without affecting the remainder of the molecule. Following the described reactions, the protecting groups may be removed and the unprotected product isolated. The protecting group employed is ideally one which may be readily synthesized, will not be affected by the reaction with the various reagents employed and may be readily removed without affecting any other functions of the molecule. It is noted that the instant protected compounds are novel and have considerable antiparasitic activity. They are included within the ambit of the instant invention. One preferred type of protecting group for the avermectin type of molecule is the tri-substituted silyl group, preferably the trialkyl silyl group. One especially preferred example, is the t butyl dimethylsilyl group. The reaction preparing the protected compound is carried out by reacting a hydroxy compound with the appropriately substituted silylhalide, preferably the silylchloride in an aprotic polar solvent such as dimethylformamide. Imidazole is added as a catalyst. The reaction is complete in from 1 to 24 hours at from 0° to 25° C. For the 5-position hydroxy group the reaction is complete in from ½ to 3 hours at from 0° C. to room temperature. This reaction is selective to the 5 position under the conditions above described and very little, if any, silylation is observed at other hydroxy substituted positions.

The silyl groups are then removed after the other reactions have been carried out. The silyl group or groups are removed by stirring the silyl compound in methanol catalyzed by a catalytic amount of an acid, preferably a sulfonic acid such as p-toluene sulfonic acid. The reaction is complete in about 1 to 12 hours at from 0° to 50° C. Alternatively, the silyl group or groups can be removed with a hydrogen fluoride-pyridine complex in an organic solvent such as tetrahydrofuran. The reaction is complete in from about 3 to 24 hours and is preferably carried out at room temperature.

Additional reactions which may be carried out to prepare the compounds of this invention are the selective removal of one of the α-L-oleandrosyl moieties (described in U.S. Pat. No. 4,206,205 to Mrozik et al.).

The reaction conditions which are generally applicable to the preparation of both the mono saccharide and aglycone involve dissolving the avermectin compound or the hydrogenated avermectin compound in an aqueous acidic non-nucleophilic organic solvent, miscible with water, preferably dioxane, tetrahydrofuran, dimethoxyethane, dimethyl formamide, bis-2-methoxyethyl ether, and the like, in which the water concentration is from 0.1 to 20% by volume. Concentrated sulfuric acid is added to the aqueous organic solvent to the extent of 0.01 to 10% (1 by volume. The reaction mixture is generally stirred at about 20–40° C., preferably at room temperature, for from 6 to 24 hours. The lower concentration of acid, from about 0.01 to 0.1% will predominately produce the monosaccharide under the above reaction conditions. Higher acid concentrations, from about 1 to 10% will predominantly produce the aglycone under the above reaction conditions. Intermediate acid concentrations will generally produce mixtures of monosaccharide and aglycone. The products are isolated, and mixtures are separated by techniques such as column, thin layer preparative and high pressure liquid chromatography, and other known techniques.

The acids which may be employed in the above process include mineral acids and organic acids such as sulfuric, hydrohalic, phosphoric, trifluoroacetic, trifluoro methane sulfonic and the like. The hydrohalic acids are preferably hydrochloric or hydrobromic. The preferred acid in the above process is sulfuric acid.

A further procedure for the preparation of the monosaccharide or aglycone of the avermectin compounds or of the hydrogenated avermectin compounds utilizes a different solvent system for the mono saccharide and the aglycone. The procedure for the preparation of the monosaccharide uses 1% acid by volume in isopropanol at from 20°–40° C., preferably room temperature, for from 6 to 24 hours. For the preparation of the aglycone, 1% acid, by volume, in methanol under the foregoing reaction conditions has been found to be appropriate.

Any strong inorganic or organic acid is appropriate for this process, and again sulfuric acid is the preferred acid.

It has also been observed that the monosaccharide is prepared during the course of the reaction used to remove the trialkylsilyl protecting group. Since acid catalysis is used to remove the protecting group, this is expected. However, in such cases, both the desired product and the monosaccharide are prepared and they can be readily separated using the above-described techniques.

In the preparation of the 4' or 4'' keto or amino substituted compounds, the avermectin starting materials are oxidized at the 4' or 4''-position to the corresponding keto compound. The procedures for the preparation of such compounds are described in U.S. Pat. No. 4,427,663 to Mrozik. During the procedure the presence of any hydroxy groups at the 5 and 23-position will require that such hydroxy groups be protected in order that they too are not oxidized. The 7-hydroxy group is very unreactive and need not be protected. The procedure used to prepare the protected intermediates are described above. The oxidation reaction is carried out in an inert solvent such as methylene chloride using oxalyl chloride or trifluoroacetic anhydride with dimethylsulfoxide as the oxidizing agent. The reaction proceeds by dissolving the oxalyl chloride or trifluoroacetic anhydride and dimethylsulfoxide (or other oxidizing reagents) in methylene chloride cooled to from $-50°$ to $-80°$ C. and adding dropwise a methylene chloride solution of the avermectin compound to be oxidized. The addition is carried out over a period of from 15 minutes to 1 hour and then triethylamine is added dropwise over a period of from 1 to 15 minutes. The reaction mixture is then allowed to warm to room temperature over a period of from ½ to 1 hour. The 4' or 4''-keto compound is isolated using techniques known to those skilled in the art.

In the next step, the 4' or 4''-keto compound is aminated to prepare the unsubstituted amino compound ($R_6=R_7=$hydrogen. The reaction is carried out in an inert solvent such as methanol at from $-10°$ to $+25°$ C. using ammonium salts and sodium cyanoboro hydride as the aminating and reducing reagents, respectively. The reaction is complete in from 15 minutes to 24 hours and the product 4''-deoxy-4''-amino compound is isolated using techniques known to those skilled in the art. Suitable ammonium salts are the acetate, propionate, benzoate and the like. The acetate is preferred.

As a variation to the foregoing amination reaction, methyl ammonium salts can be used in place of the ammonium salts to prepare the monomethyl substituted compound directly. The same reagents, salts and reaction conditions as described above can be used for such a reaction.

The substitution reaction wherein the substituent is an acyl function is carried out using an acylating reagent in the presence of a base in an inert solvent. The acylation of avermectin compounds, is fully described in U.S. Pat. No. 4,201,861 to Mrozik et al. The preferred acylating reagents are loweralkanoyl anhydrides, loweralkanoyl halides, substituted benzene sulfonyl chlorides, lower alkyl sulfonyl chlorides, and the like. The reaction is carried out in an inert solvent such as methylene chloride in the presence of a non reactive base such as pyridine or triethylamine in order to neutralize the acid produced during the course of the reaction. The reaction temperature is from $-10°$ to 25° C. and the reaction is complete in from 5 minutes to 8 hours. The product is isolated using known techniques.

The reaction for the preparation of the 4'- or 4''-deoxy-4'- or 4''-dialkylamino compounds is carried out using the alkylating reaction conditions of an excess of a carbonyl compound, preferably formaldehyde and a reducing agent such as sodium cyano borohydride, in methanol. The reaction is carried out in a solvent suitable to dissolve the organic starting material using excess aqueous formaldehyde along with the presence of a small amount of acid such as acetic acid to facilitate the reaction. The reaction is carried out at from $-10°$ to $+25°$ C. with the solution of the avermectin compound in methanol added dropwise over a period of from 30 to 60 minutes to the alkylating reagent mixture and the product is isolated using known techniques.

Further reactions of the avermectin compounds either before or after the DAST reaction are possible to prepare the compounds of this invention.

Following the preparation of the aglycone ($R_4$ is hydroxy at the 13 position), U.S. Pat. Nos. Re 32,006 and 32,034 to Chabala et al. disclose the hydroxy group displacement with a halogen using a reagent such as benzene sulfonylhalide, and the halogen is removed by reduction using a reducing agent such as trialkyltin hydride.

The hydroxy group at 5 may be alkylated following the procedures described in U.S. Pat. No. 4,200,581 to Fisher et al.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Svphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasites of the gastro intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly Musca domestica.

The compounds are also useful against insect pests of stored rains such as Tribolium sp., Tenebrio sp. and of agricultural plants such as two spotted spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture. The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formula tions may contain from 0.01 to 0.1% by weight. The capsules and boluses comprise the active ingredient admixed with a carrier vehicle such as starch, talc, magnesium stearate, or di calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being giver at one time or in divided doses over a relatively short period of time such as 1–5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as rinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

In the isolation of the avermectin compounds, which serve as starting materials for the instant processes, from the fermentation broth, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a small percent by weight, and the structural difference has negligible effect on the reaction processes and biological activities.

In particular it has been found that the starting materials for the compounds of this invention are very often prepared in a ratio of about 80% avermectin B1a or A1a and 20% avermectin B1b or A1b. Thus the preferred composition of this invention is one which contains about 80% of the "a" component and 20% of the "b" component.

The following examples are provided in order that this invention might be more fully understood; they are not to be construed as limitative of the invention.

The substituted avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed demonstrate the purity of the compounds.

In the following examples, the various starting materials therefor are avermectin compounds or derivatives of avermectin compounds. The avermectin compounds and the preparation and isolation thereof from fermentation broths are described in U.S. Pat. No. 4,310,519 issued Jan. 12, 1982. The 22,23-dihydro derivatives of avermectin compounds are described in U.S. Pat. No. 4,199,569. The aglycone and monosaccharide derivatives of avermectin compounds are described in U.S. Pat. No. 4,206,205. The 13-deoxy compounds are described in U.S. Pat. Nos. Re 32,006 and 32,034. The 4 and 4" amino compounds are described in U.S. Pat. No. 4,427,663. The acyl derivatives are disclosed in U S. Pat. No. 4,201,861 The epoxide derivatives are disclosed in U.S. Pat. No. 4,530,971. The 13 keto and amino compounds are disclosed in U.S. Pat. No. 4,579,864, and the o-alkyl compounds are disclosed in U.S. Pat. No. 4,200,581. The 13 (alkoxy)methoxy compounds are disclosed in U.S. Pat. No. 4,587,247. The following examples are being provided in order that the invention may be more fully understood. They are not to be construed as being limitative of the invention.

EXAMPLE 1

4",5-Di-O-tert-butyldimethylsilyl-avermectin B2a and/or B2b

A solution of 1.0 g of avermectin B2a and/or B2b, 0.614 g of imidazole, 0.680 mg of tert-butyldimethylsilyl chloride in 12.8 ml of anhydrous DMF was stirred at room temperature under $N_2$ for 20.5 hours. Then water and ether were added, the organic phase separated, washed repeatedly with water and concentrated in vacuo. Purification by silica gel column chromatography gave 401 mg of 4",5,23-tri-O-tert-butyldimethylsilyl-avermectin B2a and/or B2b, 437 mg of the desired 4",5-di-O-tert-butyldimethylsilyl-avermectin B2a and/or B2b, 115 mg of 5,23-di-O-tert-butyldimethylsilyl-avermectin B2a and/or B2b, and 129 mg of 5-O-tert-butyldimethylsilyl-avermectin B2a and/or B2b, all of which were characterized by their mass and/or $^1$H-NMR spectra.

EXAMPLE 2

4",5 Di-O-tert-butyldimethylsilyl-7,23-di-O-trimethylsilyl avermectin B2a and/or B2b To a solution containing 100 mg of 4",5 di-O-tert butyldimethylsilyl-avermectin B2a and/or B2b in 0.5 ml of anhydrous DMF 1.0 ml of bis(trimsthylsilyl)trifluoroacetamide was added dropwise. The reaction mixture was held 3 hours at room temperature and then evaporated in vacuo and high vacuum to a glass. This was shown to be more than 90 % pure and assigned the structure of 4",5 di-O-tert-butyldimethylsilyl-7,23-di-O-trimethylsilyl avermectin B2a and/or B2b in analogy to similar reactions. The crude product was used immediately for the next step.

EXAMPLE 3

4'',5 Di-O-tert-butyldimethylsilyl-7-O-trimethylsilyl avermectin B2a and/or B2b

A solution of 480 mg of 4'',5 di-O-tert-butyldimethylsilyl-7,23-di-O-trimethylsilyl avermectin B2a and/or B2b in 100 ml of THF, 15 ml of water, and 8.4 ml of glacial acetic acid was held at room temperature for 20 hours. Then the reaction mixture was concentrated to a smaller volume in high vacuum at room temperature. Water and EtOAc were added, and the solution was made slightly basic with $NaHCO_3$. The organic phase was separated and worked up to give 460 mg of a light yellow foam, which was characterized by its mass and $^1$H-NMR spectra as 4'',5 di-O-tert-butyldimethylsilyl-7-O-tri-methylsilyl avermectin B2a and/or B2b.

EXAMPLE 4

4'',5 Di-O-tert-butyldimethylsilyl-7-O-trimethlsilyl-23,24-dehydroavermectin B2a and/or B2b To a solution of 13.3 microL of diethylaminosulfur trifluoride (DAST) in 0.5 ml of anhydrous $CH_2Cl_2$ stirred at minus 78° C. under $N_2$ was added a solution of 100 mg of 4'',5-di-O-tert butyldimethylsilyl-7-O-trimethylsilyl avermectin B2a and/or B2b in 0.5 ml of anhydrous $CH_2Cl_2$. The reaction mixture was held 30 minutes at minus 78° C., followed by 60 minutes at minus 20° C. and 90 minutes at room temperature. The reaction product was isolated by addition of dilute $NaHCO_3$ solution and extraction with ether giving 87 mg of light colored foam. TLC analysis showed at least three reaction products. Purification by preparative silicagel layer chromatography gave 33 mg of a pure sample as white foam which was assigned the structure of 4'',5-di-O-tert-butyldimethylsilyl-7-trimethylsilyl-23,24-dehydroavermectin B2a and/or B2b by its mass and $^1$H NMR spectra. The structure was confirmed by further spectral investigation of the deprotected compound.(-See Example 5).

EXAMPLE 5

23,24-Dehydroavermectin B2a and/or B2b

A solution of 33 mg of 4'',5-di-O-tert-butyldimethylsilyl-7-O-trimethylsilyl-23,24-dehydroavermectin B2a and/or B2b in 2.0 ml of an anhydrous hydrogen fluoride pyridine tetrahydrofuran mixture, prepared by mixing 14.0 ml of THF, 4.0 ml of pyridine and 2.0 ml of commercial HF pyridine (consisting of 70 % HF and 30 % of pyridine, supplied by Aldrich Chemical Company) was kept at room temperature for two days. Then the reaction mixture was poured into dilute aqueous sodium bicarbonate solution and extracted with EtOAc to give 27 mg of 23 24-dehydroavermectin B2a and/or B2b as a glass, which was fully characterized by its UV spectrum, EI and FAB mass spectra, and $^1$H-, and $^{13}$C-NMR spectra including $^1$H-"COSY" and $^{13}$C-APT.

EXAMPLE 6

23,24-Dehydroavermectin A2a and/or A2b

When avermectin A2a and/or A2b is reacted in accordance to the procedures described in examples 1, 2, 3, 4, and 5, 23,24-dehydroavermectin A2a and/or A2b is obtained, which can be characterized by its mass spectrum and $^1$H-, and $^{13}$C-NMR spectra.

EXAMPLE 7

23,24 -Dehydro-13-deoxyavermectin B2a and/or B2b aglycone

When 13-deoxyavermectin B2a and/or B2b aglycone is reacted in accordance to the procedures described in examples 1, 2, 3, 4, and 5, then 23,24-dehydro-13-deoxyavermectin B2a and/or B2b aglycone is obtained, which can be characterized by its mass spectrum and $^1$H , and $^{13}$C-NMR spectra.

Example 8

5-O-t-Butyldimethylsilyl-23,24-dehydroavermectin B2a and/or B2b

A solution of 130 mg of 23,24-dehydroavermectin B2a, 68 mg of imidazole, and 61 mg of tert-butyldimethylsilyl chloride in 1.5 ml of DMF is stirred at room temperature for 45 min. The reaction mixture is then poured into water. The product is extracted with ether; the extract is washed with water, dried and concentrated in vacuo to a light foam. Purification by preparative silica gel thin layer chromatography with $CH_2Cl_2$-EtOAc 85:15 solvent mixture gives 5-O-t-butyldimethylsilyl-23,24-dehydroavermectin B2a and/or B2b, which is characterized by NMR and mass spectra.

Example 9

5-O-t-Butyldimethylsilyl-23,24-dehydro-4''-oxoavermectin B2a and/or B2b

A solution of 57 mg (0.04 ml) of oxalyl chloride in 1 ml of $CH_2Cl_2$ is stirred under $N_2$ at $-60°$ C. To this is added a solution of 70 mg (0.065 ml) of dimethylsulfoxide in 0.4 ml of $CH_2Cl_2$, followed by a solution of 200 mg of 5-O-t-butyldimethylsilyl-23,24-dehydroavermectin B2a/B2b in 1.2 ml of $CH_2Cl_2$. It is stirred at $-60°$ C. for 30 min. Then 0.3 ml of triethylamine is added. After 5 minutes the reaction mixture is allowed to warm up to room temperature during the next hour. Then the mixture is poured into water and extracted with ether. The extract is washed with water, dried, and concentrated in vacuo to a yellow foam. The 5-O-t-butyldimethylsilyl-23,24-dehydro-4''-oxoavermectin B2a/B2b is identified by NMR and mass spectra and used without further purification as starting material for chemical reactions.

Example 10

4''-Deoxy-4''-methylamino-5-O-t-butyldimethylsilyl-23,24-dehydroavermectin B2a and/or B2b A solution of 200 mg of 5-O-t-butyldimethyl-silyl-23,24-dehydro 4'' oxo avermectin B2a/B2b and 190 mg of $CH_3NHOAc$ in 3 ml of MeOH is stirred at room temperature for 15 minutes. Then 12 mg of $NaCNBH_3$ is added. After 1 hour the reaction mixture is poured into aqueous dilute $Na_2CO_3$ solution. The product is extracted with EtOAc, and the extract is washed with water, dried, and concentrated in vacuo to a yellow foam. The product is purified by preparative silica gel layer chromatography with a $CH_2Cl_2$-MeOH 93:7 solvent mixture, and is identified by NMR and mass spectra as 4''-deoxy-4''-methylamino-5-O-t-butyldimethylsilyl-23,24-dehydroavermectin B2a/B2b

Example 11

4"-Deoxy-4"-methylamino-23,24-dehydroavermectin B2a and or B2b

A solution of 100 mg of 4"-deoxy-4" methylamino-5O-t-butyldimethylsilyl-23,24-dehydroavermectin B2a/B2b and 100 mg of p toluenesulfonic acid monohydrate in 10 ml of MeOH is stirred at room temperature for 30 minutes, and then poured into dilute aqueous $NaHCO_3$ solution. The product is extracted with EtOAc, washed with water and dried over $MgSO_4$, concentrated in vacuo, and purified by preparative silicagel layer chromatography with a $CH_2Cl_2$-MeOH 95:5 solvent mixture. It is identified by NMR and mass spectra as 4"-deoxy-4"-methylamino-23,24-dehydroavermectin B2a/B2b.

EXAMPLE 12

5-O-tert-Butyldimethylsilyl-23,24-dehydro-4"-oxoavermectin B2a and/or B2b (4-methyl)semicarbazone A solution of 3.0 ml of MeOH containing 5O-tert-butyldimethylsilyl-23,24-dehydro-4" oxo-aver mectin B2a/B2b ( 50 mg ), 4-methylsemicarbazide hydrochloride ( 17 mg ), and sodium acetate ( 15 mg) is stirred at room temperature for 2 hours. Then addition of 4 ml of water, extraction with ether, washing with water, drying and concentration in vacuo gives the crude product. Purification by preparative silicagel layer chromatography with a $CH_2Cl_2$-MeOH solvent mixture gives pure 5-O-tert-butyldimethylsilyl-23,24-dehydro-4"-oxoavermectin B2a and/or B2b (4 methyl)semicarbazone, which is characterized by its mass and $^1$H-NMR spectra.

EXAMPLE 13

23,24-Dehydro-4"-oxoavermectin B2a and/or B2b (4-methyl)semicarbazone

A solution of 35 mg of 5-O-tert-butyldimethylsilyl-23,24-dehydro4"-oxoavermectin B2a and/or B2b (4 methyl)semicarbazone in 3.5 ml of MeOH containing 1 % of p-toluenesulfonic acid monohydrate is held at room temperature for 60 minutes. Addition of aqueous $NaHCO_3$ solution, extraction with ether, washing with water, drying and concentration in vacuo gives crude product. Purification by preparative silicagel layer chromatography using a $CH_2Cl_2$-MeOH solvent mixture affords pure 23,24-dehydro-4"-oxoavermectin B2a and/or B2b (4 methyl)semi-carbazone, which is characterized by its mass and $^1$H-NMR spectra.

EXAMPLE 14

10,11-Dihydroavermectin B2a/B2b

A solution of 870 mg avermectin B2a/B2b in 25 mL of absolute ethanol and 100 mg of 5% Pd/C was stirred at room temperature under one atmosphere pressure of hydrogen. After an uptake of 1.5 molar equivalent of hydrogen, the catalyst was removed by filtration. HPLC analysis using a reverse phase $C_{18}$ column and a methanol-water liquid system indicated the composition of the mixture to be 20% avermectin B2a/B2b, 50% 10,11-dihydroavermectin B2a/B2b, 30% 3,4-dihydroavermectin B2a/B2b, and 10% 3,4,10,11-tetrahydroavermectin B2a/B2b. Preparative HPLC using a reverse phase $C_{18}$ column and a methano-water system gave pure 10,11-dihydro avermectin B2a and/or B2b which was characterized by its $^1$H NMR and its mass spectra.

EXAMPLE 15

23,24-Dehydro-10,11-dihydroavermectin B2a and/or B2b

When 1.0 g of 10,11 dihydroavermectin B2a and/or B2b is reacted consecutively according to the procedures fully described in examples 1, 2, 3, 4, and 5, 23,24-dehydro 10,11 dihydroavermectin B2a and/or B2b is obtained, which is characterized by its mass and $^1$H-NMR spectra.

EXAMPLE 16

5-O-tert-Butyldimethylsilyl-23,24-dehydro-10,11-dihydro-10-hydroxyavermectin B2a/B2b To a solution of 500 mg of 5-O-tert-butyl dimethylsilyl-23,24-dehydroavermectin B2a/B2b in 10 mL of acetone and 1.0 mL of water is added 110 mg of N-bromoacetamide in one portion. The mixture is stirred in the dark at 20° C. for 1 h, and worked up by addition of water and extraction with ether or dichloromethane. The solvent is removed in vacuo and the residual solid is purified by preparative thick layer silica gel chromatography using a 1:1 hexane: ethyl acetate solvent system to afford crude 5-O-tert-butyldimethylsilyl-11-bromo-23,24-dehydro-10,11-dihydro-10-hydroxyavermectin B2a/B2b. This intermediate product is dissolved in 6 mL of toluene, and 0.4 mL of tri n butyltin hydride is added. The mixture is heated at 100° C. under an atmosphere of nitrogen for 2 hours. Column chromatography on silica gel with dichloromethane followed by 1:1 hexane: ethyl acetate provides an initial separation of the product from the tin compounds. Final purification of the product is achieved by HPLC on a C-18 reverse phase column using a methanol water liquid phase to afford pure 5-O-tert-butyldimethylsilyl-23,24-dehydro-10,11-dihydro10-hydroxyavermectin B2a/B2b, which is characterized by its NMR and mass spectra.

EXAMPLE 17

5-O-tert-Butyldimethylsilyl-23,24-dehydro-10,11-dihydro-10-hydroxy-4"-O-trimethylsilylavermectin B2a/B2b To 2.0 g of 5-O-tert-butyldimethylsilyl 23,24 dehydro 10,11-dihydro 10 hydroxyavermectin B1a/B1b is added 20 mL of freshly distilled dichloro methane, 4 mL of (4A sieve dried) N,N dimethyl formamide, and 1.0 mL of freshly distilled triethyl amine. To this mixture, after cooling to 0° C., is added 0.41 mL of chlorotrimethylsilane. The reaction mixture is stirred at 20° C. for 2 hours. The reaction mixture is then quenched with 300 mL of water and 60 mL of a saturated sodium bicarbonate solution. Extraction with dichloromethane and evaporation of the solvent yields the product as a solid. Purification by chromatography on silica gel using 3:1 hexane : EtOAc affords 5-O-tert-butyldimethylsilyl-23,24-dehydro-10,11-dihydro-10-hydroxy-4"-O-trimethylsilylavermectin B2a/B2b which is characterized by its NMR and mass spectra.

EXAMPLE 18

5-O-tert-Butyldimethylsilyl-23,24-dehydro-10,11-dihydro-10-fluoroavermectin B1a/B1b A solution of 1.68 g of 5-O-tert-butyldimethylsilyl-23,24-dehydro-10,11-dihydro-10-hydroxy-4"-O-trimethylsilylavermectin B2a/B2b in 20 mL of freshly distilled dichloromethane under nitrogen is cooled to −78° C. To this mixture is added dropwise 0.23 mL of diethylaminosulfur trifluoride. After 1 hour at −78° C. the reaction mixture is quenched with 5 mL of a 7% aqueous sodium carbonate solution. Extraction with dichloromethane from the aqueous workup affords a mixture of crude products. This mixture is dissolved in 20 mL of THF: water (9:1) and 125 mg of p toluenesulfonic acid monohydrate is added in one portion. After exactly 15 min at 20° C. the reaction is quenched by addition of 5 mL of a saturated aqueous sodium bicarbonate solution. Dichloromethane extraction of the aqueous workup affords the crude product (two major components by TLC analysis). Chromatographic purification on silica gel using hexane: ethyl acetate (2:1) affords 5-O-tert-butyldimethylsilyl 23,24 dOhydro-10,11-dihydro-10-fluoroavermectin B2a/B2b and 5-O-tert-butyldimethylsilyl-23,24-dehydro-10,11-dihydro-10-hydroxyavermectin B2a/B2b, which were characterized by their NMR and mass spectra.

EXAMPLE 19

23,24-Dehydro-10,11-dihydro-10-fluoroavermectin B2a/B2b When
5-O-tert-butyldimethylsilyl-23,24-dehydro-10,11-dihydro-10-fluoroavermectin B2a/B2b is treated with a solution of anhydrous hydrogen fluoride - pyridine tetrahydrofuran as fully described in example 5 one obtains
23,24-dehydro-10,11-dihydro-10-fluoroavermectin B2a/B2b which is characterized by its mass spectrum and $^1$H and $^{13}$C-NMR spectra.

EXAMPLE 20

5-O-tert-Butyldimethylsilyl-avermectin B2a/B2b aglycone

A solution containing 400 mg of avermectin B2a/B2b aglycone (prepared as decribed in U.S. Pat. No. 4,206,205) and 544 mg of imidazole in 8.0 ml of dimethylformamide was stirred at room temperature until all was in solution. Then 600 mg of tert-butyldimethylsilyl chloride was added in one portion and the reaction mixture was stirred for an additional 50 minutes at room temperature, when water was added. The reaction product was isolated by extraction with ether, washing of the extracts several times with water, then saturated aqueous sodium chloride solution, drying over magnesium sulfate, and concentration to 800 mg of solid residue. Purification by preparative silica gel layer chromatography with 5% tetrahydrofuran in methylene chloride gave 330 mg of 5O-tert-butyldimethylsilyl avermectin B2a/B2b aglycone, which was characterized by its mass and NMR spectra.

EXAMPLE 21

5-O-tert-Butyldimethylsilyl-7,13,23-tri-O-trimethylsilylavermectin B2a/B2b aglycone A solution of 640 mg of 5-0 tert butyldimethylsilyl avermectin B2a/B2b aglycone in 7.5 ml of anhydrous dimethylformamide is stirred at room temperature while 15 ml of bis(trimethylsilyl)-trifluoroacetamide is added dropwise. After standing an additional 3 hours the reaction mixture is evaporated in high vacuum to a glass, which is characterized by its mass and NMR spectra as 5-O-tert-butyldimethylsilyl-7,13,23-tri-O-trimethyl-silylavermectin B2a/B2b aglycone. The crude product is used for the next step without further purification.

EXAMPLE 22

5-O-tert-Butyldimethylsilyl-7-O-trimethylsilylavermectin B2a/B2b aglycone

A solution of 354 mg of 5-O-tert butyl dimethylsilyl-7,13,23-tri-O-trimethylsilylavermectin B2a/B2b aglycone in 100 ml of tetrahydrofuran, 15 ml of water, and 8.4 ml of glacial acetic acid is kept at room temperature for 20 hours, when the solution is concentrated in vacuo to a small volume in a water bath of 35° C. Water and ethyl acetate are added and the solution made slightly basic with sodium carbonate. The organic phase is separated, dried, and concentrated in vacuo to a light yellow foam, which is characterized by its mass and NMR spectra as 5-O-tert-butyldimethylsilyl-7-O-trimethylsilylavermectin B2a/B2b aglycone

EXAMPLE 23

5-O-tert-Butyldimethylsilyl-23,24-dehydro-13-deoxy-13-fluoro-7-O-trimethylsilylavermectin B2a/B2b aglycone To a solution of 40 μL of diethylaminosulfur trifluoride (DAST) in 1.5 mL of anhydrous methylene chloride stirred at −78° C. under a blanket of nitrogen, a solution of 100 mg of 5-O-tert-butyldimethylsilyl-7-O-trimethylsilylavermectin B2a/B2b aglycone in 1.5 mL of anhydrous methylene chloride is added dropwise. Subsequently the reaction mixture is kept for 30 minutes at −78° C., followed by 60 minutes at −20° C., and 90 minutes at room temperature. Then dilute aqueous sodium bicarbonate solution is added slowly with ice cooling, and the mixture is extracted with ether, the ether extract is washed with water, dried, and concentrated in vacuo and under high vacuum to a light foam. Purification by preparative silica gel layer chromatography gives 5-O-tert-butyldimethylsilyl-23,24-dehydro-13-deoxy-13-fluoro-7-O-trimethylsilylavermectin B2a/B2b aglycone, which is characterized by its mass and NMR spectra. This product is obtained as a mixture of the two C-13 epimeric 13-alpha and 13-beta fluorocompounds.

EXAMPLE 24

23,24-Dehydro-13-deoxy-13--fluoroavermectin B2a/B2b aglycone

A solution of 21.6 mg of 5 0 tert-butyldimethylsilyl-23,24-dehydro-13-deoxy-13-fluoro-7-O-trimethylsilylavermectin B2a/B2b aglycone in 2.0 mL of an anhydrous hydrogen fluoride - pyridine-tetrahydrofuran mixture prepared as described in Example 5 is held at room temperature for 48 hours. Then the reaction mixture is poured into dilute aqueous sodium bicarbonate solution and extracted with ethyl acetate, washed with water, dried, and evaporated to a light colored glass. Purification by preparative silica gel layer chromatography gives the two C-13 epimeric 23,24-dehydro-13-deoxy-13-fluoroavermectin B2a/B2b aglycones, which are characterized by their mass and NMR spectra.

What is claimed is:

1. A compound having the formula:

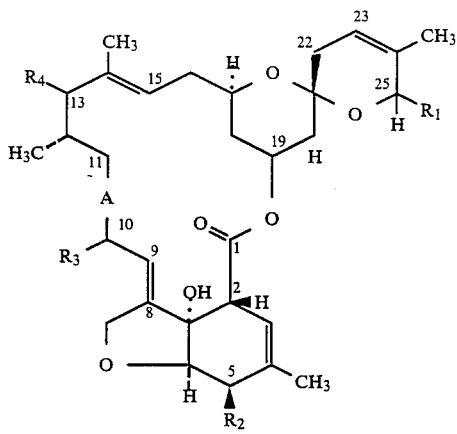

wherein A represents a single bond or a double bond;
$R_1$ is iso-propyl or sec-butyl;

$R_2$ is hydroxy, oxo, loweralkoxy, or triloweralkylsilyl substituted hydroxy;

$R_3$ is hydrogen, hydroxy, halogen, or oxo or triloweralkylsilyl substituted hydroxy, however $R_3$ is present only when A represent a single bond;

$R_4$ is hydrogen, hydroxy, halogen, triloweralkylsilyl substituted hydroxy,

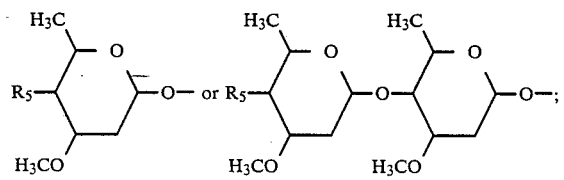

$R_5$ is hydroxy, triloweralkylsilyl substituted hydroxy, oxo, $-NR_6R_7$ or

$R_6$ and $R_7$ are independently hydrogen, loweralkyl, or loweralkanoyl.

2. The compound of claim 1 wherein A is a single or a double bond;
$R_1$ is isopropyl or sec-butyl;
$R_2$ is hydroxy;
$R_3$ is hydrogen, halogen, hydroxy or oxo;
$R_4$ is hydrogen, hydroxy, halogen, 4'-$R_5$-(α-oleandrosyloxy), 4''-$R_5$-[(α-L-oleandrosyl)-α-L-(oleandrosyloxy)]; and
$R_5$ is hydroxy, amino, loweralkylamino or diloweralkylamino.

3. The compound of claim 1 where $R_1$, $R_2$ and $R_3$ are as defined in claim 1 and $R_4$ is halogen.

4. The compound of claim 3 where $R_4$ is fluorine.

5. The compound of claim 1 selected from the group consisting of 23,24-dehydro avermectin B2a and B2b.

6. The compound of claim 1 selected from the group consisting of 23,24-dehydro avermectin A2a and A2b.

7. The compound of claim 1 selected from the group consisting of 23,24-dehydro-13-deoxy avermectin B2a and B2b aglycone.

8. The compound of claim 1 selected from the group consisting of 23,24-dehydro-10.11-dihydro-10-fluoroavermectin B2a and B2b.

9. The compound of claim 1 selected from the group consisting of 23,24-dehydro-4''-deoxy-4''-methylaminoavermectin B2a and B2b.

10. The compound of claim 1 selected from the group consisting of 4''-oxo-23,24-dehydro avermactin B2a and B2b 4-methyl semicarbazone.

11. The compound of claim 1 selected from the group consisting of 23,24-dehydro-13-deoxy-13-fluoro avermectin B2a and B2b aglycone.

12. A method for the treatment of parasitic infections of animals which comprises administering to an animal infected with parasites an effective amount of a compound of claim 1.

13. A composition useful for treating animals infected with parasites and for areas infected with insect pests which comprises an inert carrier and an effective amount of a compound of claim 1.

14. A method for the treatment of insect pests of plants which comprises applying to plants infected with such insect pests or the soil in which they grow, an effective amount of a compound of claim 1.

15. A process for the preparation of the compounds of claim 1 which comprises treating a compound having the formula:

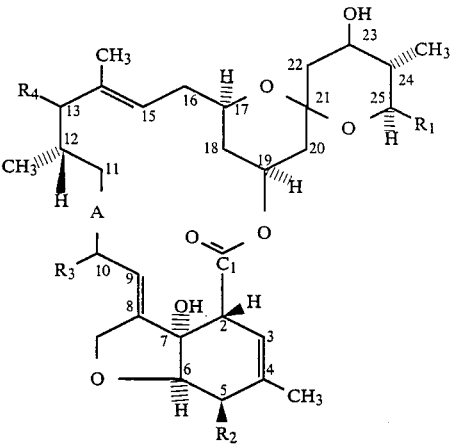

wherein A, $R_1$, $R_2$, $R_3$ and $R_4$ are as defined in claim 1, with diethylamino sulfurtrifluoride initially at from $-50°$ to $-100°$ C. followed by reaction at room temperature.

* * * * *